US009937499B2

(12) United States Patent
González Fernández et al.

(10) Patent No.: US 9,937,499 B2
(45) Date of Patent: Apr. 10, 2018

(54) HANDGRIP TEST STRIP EJECTOR (71) Applicant: Roche Diabetes Care, Inc., Indianapolis, IN (US)

(72) Inventors: Andrea González Fernández, Barcelona (ES); Bartomeu Ventayol Femenias, Barcelona (ES)

(73) Assignee: Roche Diabetes Care, Inc., Indianapolis, IN (US)

( * ) Notice: Subject to any disclaimer, the term of this patent is extended or adjusted under 35 U.S.C. 154(b) by 146 days.

(21) Appl. No.: 15/153,889

(22) Filed: May 13, 2016

(65) Prior Publication Data
US 2016/0250641 A1    Sep. 1, 2016

Related U.S. Application Data (63) Continuation of application No. PCT/EP2014/075462, filed on Nov. 25, 2014.

(30) Foreign Application Priority Data

Nov. 27, 2013 (EP) ..................... 13005518
Jul. 15, 2014 (EP) ..................... 14002428

(51) Int. Cl.
*B01L 9/00* (2006.01)
*A61B 5/145* (2006.01)
(Continued)

(52) U.S. Cl.
CPC ............ *B01L 9/52* (2013.01); *A61B 5/14532* (2013.01); *B25G 1/102* (2013.01); *B25G 3/18* (2013.01);
(Continued)

(58) Field of Classification Search
CPC ................. B01L 9/52; B01L 2200/082; B01L 2200/085; A61B 5/14532;
(Continued)

(56) References Cited

U.S. PATENT DOCUMENTS 5,424,035 A    6/1995 Hoenes et al.
7,240,565 B2   7/2007 Eisenmann et al.
(Continued)

FOREIGN PATENT DOCUMENTS

CN    1616316 A     5/2005
CN    101288592 A    10/2008
(Continued)

OTHER PUBLICATIONS

China Patent Application 201480065023.9 First Office Action dated Jan. 9, 2017, 8 pages.
(Continued)

*Primary Examiner* — Robert R Raevis
(74) *Attorney, Agent, or Firm* — Woodard, Emhardt, Moriarty, McNett & Henry LLP (57) ABSTRACT

In a first aspect, the present invention provides a handgrip configured to extract an analysis strip from a groove of an analyser. The handgrip comprises a casing piece configured to be attached with the analyser, and a retaining piece having a retaining portion. The retaining piece is movable with respect to the casing piece in such a way that the retaining portion is movable in a first direction from a proximal position to a distal position relative to the casing piece. The retaining portion is configured to retain the analysis strip during at least part of its movement from the proximal to the distal position, and to avoid retaining the analysis strip at least when the retaining portion is in any of the proximal and distal positions.

15 Claims, 7 Drawing Sheets

(51) Int. Cl.
  *B25G 3/18* (2006.01)
  *B25G 1/10* (2006.01)
  *G01N 33/487* (2006.01)
  *G01N 33/49* (2006.01)

(52) U.S. Cl.
  CPC ......... *G01N 33/4875* (2013.01); *G01N 33/49* (2013.01); *A61B 2560/0443* (2013.01); *A61B 2562/0295* (2013.01); *B01L 2200/082* (2013.01)

(58) Field of Classification Search
  CPC .... A61B 2560/0443; A61B 2562/0295; B25G 3/18; B25G 1/102; G01N 33/4875; G01N 33/49
  USPC ........... 73/61.41, 61.43, 61.48, 61.71, 61.72, 73/64.56, 863, 864.81, 864.91, 431, 73/432.1; 422/68.1, 82.05–82.11, 500, 422/563; 436/66, 67, 174, 180; 435/4–40.52; 356/39–42; 600/301, 600/322–340, 347
  See application file for complete search history.

(56) References Cited

U.S. PATENT DOCUMENTS

| | | |
|---|---|---|
| 8,801,632 B2 | 8/2014 | Chan |
| 2005/0061700 A1 | 3/2005 | Windus-Smith et al. |
| 2005/0256382 A1 | 11/2005 | Eisenmann et al. |
| 2006/0133956 A1* | 6/2006 | Hamanaka ................ B01L 9/52 422/68.1 |
| 2007/0183925 A1 | 8/2007 | Schabbach |
| 2008/0262386 A1 | 10/2008 | Haar et al. |
| 2012/0199601 A1* | 8/2012 | Sawa ............... G01N 33/48757 221/1 |
| 2012/0252133 A1 | 10/2012 | Faulkner et al. |

FOREIGN PATENT DOCUMENTS

| | | |
|---|---|---|
| CN | 102735724 A | 10/2012 |
| WO | WO 2015/078832 A1 | 6/2015 |

OTHER PUBLICATIONS

International Patent Application PCT/EP2014/075462 International Search Report and Written Opinion dated Feb. 17, 2015, 9 pages.

* cited by examiner

HANDGRIP TEST STRIP EJECTOR

CROSS-REFERENCE TO RELATED APPLICATION

This application is the continuation of International Application No. PCT/EP2014/075462, filed Nov. 25, 2014, which claims the benefit of European Application No. 13005518.9 filed Nov. 27, 2013 and European Application No. 14002428.2 filed Jul. 15, 2014, the entire disclosures of which are hereby incorporated by reference.

The present invention relates to handgrips configured to extract an analysis strip from a groove of an analyser.

BACKGROUND ART

Analysers for analysing analysis strips are widely used. Some analysers have a groove for receiving an analysis strip. Such strips are configured to receive and retain a body fluid (e.g. blood) sample to be analysed. The groove into which the strip is to be inserted to carry out an analysis (of e.g. glucose in blood) is typically arranged on an end region of the analyser. Once the strip has been used (so that it still contains a body fluid sample), the strip has to be removed from the analyser. Removal of the strip by hand is not recommended in order to e.g. avoid risk of infection.

Analysers are known which do not have any kind of system for ejecting strips. In this case, an operator (doctor, nurse, etc.) can remove a used strip from the analyser by gripping and pulling the strip by hand. But, as commented before, this way of extracting the strip is not recommended at all.

Analysers are known having a system for automatically ejecting strips integrated within the analyser, in such a way that all the components of the analyser (including the ejection system) are covered and/or protected by a common casing of the analyser. These ejection systems are typically based on rather complex configurations/mechanisms which are internal to the main casing of the analyser. Thus, if e.g. the ejection system needs to be repaired, the main casing of the analyser has to be dismounted, in which case other components, such as sensitive electronic elements, may be exposed to a certain risk of damage.

Other known ejection systems for an analyser are based on having a small wheel outside the main casing of the analyser and near the groove, the wheel being arranged to make a certain pressure on the strip (when it is inserted in the groove). In this case, the strip is ejected by an operator directly acting on (touching) the wheel to make it rotate, such that this rotation of the (pressing) wheel causes the strip to move out of the groove and, thus, to be ejected from the groove. A drawback of this approach may be that the operator has to act (by touching the wheel) on a position very close to the strip, so that the risk of infection may still be significant.

The present invention aims at providing a solution overcoming at least some of the previously commented problems/limitations.

SUMMARY OF THE INVENTION

In a first aspect, the present invention provides a handgrip configured to extract an analysis strip from a groove of an analyser. The handgrip comprises a casing piece configured to be attached with the analyser, and a retaining piece having a retaining portion. The retaining piece is movable with respect to the casing piece in such a way that the retaining portion is movable in a first direction from a proximal position to a distal position relative to the casing piece. The retaining portion is configured to retain the analysis strip during at least part of its movement from the proximal to the distal position, and to avoid retaining the analysis strip at least when the retaining portion is in any of the proximal and distal positions.

With this handgrip suitably coupled to an analyser, an analysis strip may be easily inserted into a groove of the analyser when the retaining portion of the retaining piece is in its proximal position, since the retaining portion is configured to avoid retention of the strip when it is in the proximal position. This means that no opposition is presented by the retaining portion to the insertion of the strip into the groove in said proximal position.

Once inserted and processed by the analyser, the strip can be easily extracted from the groove by moving the retaining piece for causing movement of the retaining portion towards its distal position. As the retaining portion retains (or holds) the strip during at least part of said movement, pulling of the strip may be caused until it is taken out of the groove.

Once the strip has been taken out of the groove, then the retaining portion reaches its distal position and the strip is released because the retaining portion is configured to avoid retention of the strip also in said distal position. Ejection of the strip is therefore finally caused.

A handgrip for easily extracting an analysis strip from an analyser is therefore provided.

This proposed configuration is based on "externally" gripping and pulling the strip away from the groove (by the retaining portion). This approach may provide a significant versatility in terms of e.g. providing different possibilities with respect to manufacture and/or use of the handgrip. For example, the handgrip could be fabricated as a removable handgrip, such that the handgrip may be removed (uncoupled) from the analyser in a relatively easy manner. This way, a damaged handgrip may be easily replaced by a new or at least not damaged handgrip.

Alternatively, the handgrip could be fabricated integrated with the analyser, in such a way that the analyser and the handgrip may constitute a single product.

In any case, the handgrip, either a separate piece or a part of the analyser, may be repaired without necessity of dismounting the main casing of the analyser, such that other more sensitive components (such as e.g. electronic components) are not exposed to a certain risk of damage. Also, since the handgrip has a rather simple configuration and is external to the main casing of the analyser, the reparation of the handgrip may be easier and cheaper with respect to at least some prior art ejection systems.

Moreover, this approach may permit a variety of configurations in which the retaining piece may be moved (between the proximal and distal positions) by a corresponding operator (e.g. doctor, nurse, etc.) acting on positions significantly away from the strip. This way, the risk of infection may be significantly minimized.

In some examples, the retaining portion may comprise a pressing arrangement configured to exert pressure to the analysis strip, thereby causing the retention of the analysis strip, during the at least part of the movement of the retaining portion from the proximal to the distal position. This pressing arrangement may be further configured to avoid exerting pressure to the analysis strip, thereby causing the avoidance of retention of the analysis strip, at least when the retaining portion is in any of the proximal and distal positions.

In alternative configurations, one or more elastic (instead of pressing) arrangements may be used to achieve the same or similar functionalities (retention of the analysis strip and avoidance of retention of the analysis strip).

In particular examples, the pressing arrangement may comprise a first and a second pressing member facing each other and defining a path having a distance between them, said path being perpendicular to the first direction. These first and second pressing members may be configured to reduce the distance between them, thereby causing the exertion of pressure to the analysis strip, during the at least part of the movement of the retaining portion from the proximal to the distal position. These first and second pressing members may be configured to increase the distance between them, thereby causing the avoidance of exertion of pressure to the analysis strip, at least when the retaining portion is in any of the proximal and distal positions.

In alternative configurations, other numbers of pressing members (more than two pressing members) may be used for exerting the abovementioned pressure to the strip.

In particular examples, the first and second pressing members may be arranged in such a way that the abovementioned distance reduction causes the exertion of pressure to the analysis strip at corresponding first and second lateral regions of the analysis strip, during the at least part of the movement of the retaining portion from the proximal to the distal position.

Alternatively to having lateral pressing members, the pressing arrangement may be based on at least an upper pressing member and a lower pressing member adapted to apply the pressure to the analysis strip for the retaining piece to cause a suitable retention of the strip.

In even more particular examples, each of the first and second pressing members may comprise a pressing surface by which the first and second pressing members exert the pressure to the analysis strip. Each of these pressing surfaces may be a rough surface for improving the retention of the strip.

In some examples, at least one of the first and second pressing members may be a flexible member configured to be flexed to a compressed position for causing the distance reduction during the at least part of the movement of the retaining portion from the proximal to the distal position, and to be flexed to a relaxed position for causing the distance increase at least when the retaining portion is in any of the proximal and distal positions.

In more particular implementations, both the first and second pressing members may be flexible members configured to be flexed to a compressed position for causing the distance reduction during the at least part of the movement of the retaining portion from the proximal to the distal position, and to be flexed to a relaxed position for causing the distance increase at least when the retaining portion is in any of the proximal and distal positions.

According to some examples, the casing piece may comprise a guiding piece for each flexible pressing member respectively. Besides, each guiding piece may be configured to guide its corresponding flexible pressing member to the compressed position for causing the distance reduction (during the at least part of the movement of the retaining portion from the proximal to the distal position), and to guide its corresponding flexible pressing member to the relaxed position for causing the distance increase (at least when the retaining portion is in any of the proximal and distal positions).

In configurations of the handgrip, the casing piece may be configured to be removably attached with the analyser in a press-fitting manner.

In particular, the casing piece may comprise at least two flanges configured to press against corresponding end sides of the analyser respectively, in such a way that the analyser can be press-fitted within the casing piece. In alternative examples, more than two flanges can be considered and some of them can be configured to press against other sides (e.g. lateral sides) of the analyser.

According to examples of the handgrip, the casing piece may comprise a sheet-shaped portion connecting the at least two flanges and being configured to at least partially cover a rear/bottom side of the analyser when the analyser is press-fitted within the casing piece.

In examples of the handgrip, the retaining piece may comprise a sheet-shaped portion slidably coupled to the sheet-shaped portion of the casing piece. This slidably coupling between the sheet-shaped portion of the retaining piece and the sheet-shaped portion of the casing piece may be based on e.g. a rail based mechanism. An aspect of these examples may be that an operator (e.g. doctor, nurse, etc.) may eject the strip by acting on (touching) the sheet-shaped portion of the retaining piece, which is significantly away from the strip/groove. The risk of infection is thus significantly minimized.

In still more particular examples, the sheet-shaped portion of the retaining piece may have an external rough surface. An aspect of this feature may be that the operator's hand (or fingers) may act on the sheet-shaped portion of the retaining piece in an improved manner.

An analyser may also be provided comprising a groove for inserting an analysis strip and a handgrip configured to extract the analysis strip from the groove. This handgrip may be any of the previously described handgrips. In some examples, this analyser may be provided with the analysis strip inserted in the groove.

Any of the previously commented examples of the handgrip may be made of plastic. More particularly, any of the examples may be made of Acrylonitrile butadiene styrene (ABS). This way, the handgrip may be significantly cheap to manufacture while providing a significant efficiency.

Preferably, in any of the previously described examples, the handgrip may be a removable handgrip, which may be based on e.g. the above mentioned handgrip casing configured to receive the analyser in a press fitting manner.

BRIEF DESCRIPTION OF THE DRAWINGS

Particular examples of the present invention will be described in the following by way of non-limiting examples, with reference to the appended drawings, in which.

DETAILED DESCRIPTION OF EXAMPLES OF THE INVENTION

In the following description, numerous specific details are set forth in order to provide a thorough understanding of examples of the present invention. It will be understood by one skilled in the art however, that examples of the present invention may be practiced without some or all of these specific details. In other instances, well known elements have not been described in detail in order not to unnecessarily obscure the description of the present invention.

In some cases, the same reference numbers have been used to indicate the same or similar elements shown in different Figures.

Figure 1:
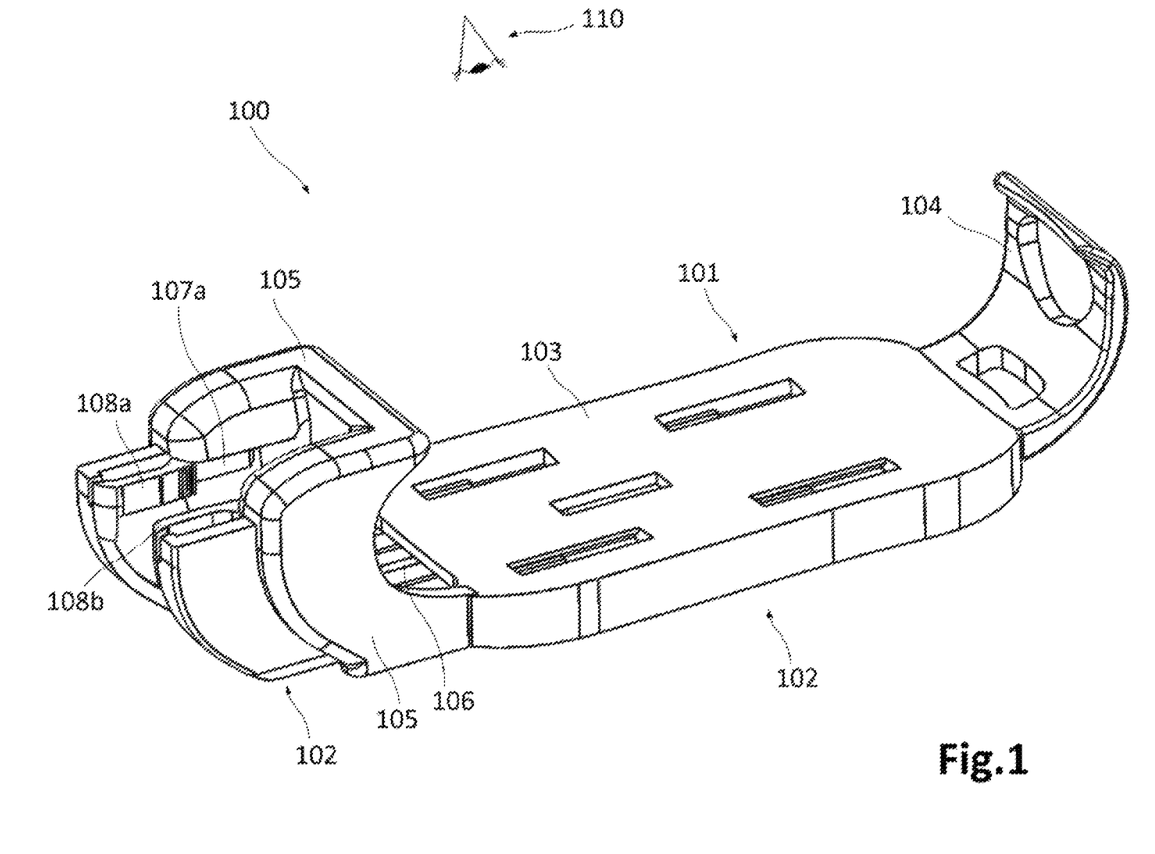
FIG. 1 schematically represents a perspective view of a handgrip according to an example, wherein its retaining portion is shown in its distal position.
Figure 2:
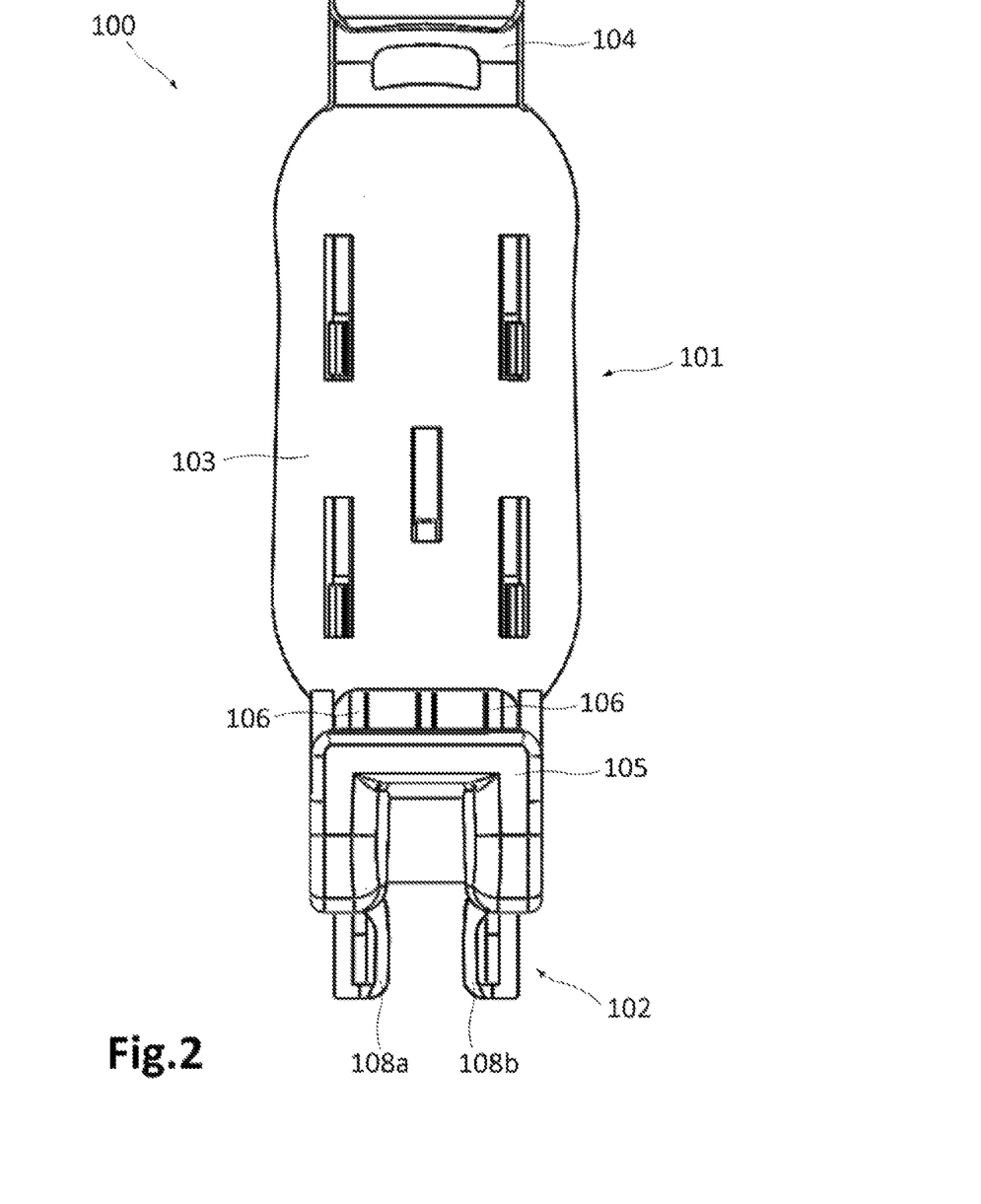
FIG. 2 schematically represents a plan view of a handgrip similar to the one shown in FIG. 1, with its retaining portion shown in its distal position.

FIG. 1 schematically represents a perspective view of a handgrip 100 according to an example. FIG. 2 schematically represents a plan view of a handgrip 100 similar to the one shown in FIG. 1. The handgrip 100 is shown in these Figures comprising a casing piece 101 and a retaining piece 102, the retaining piece 102 having a retaining portion 108a, 108b being arranged in its distal position in these particular views.

The plan view of FIG. 2 may be considered as taken from a top point of vision 110 as indicated in FIG. 1.

The casing piece 101 is shown in both Figures comprising two flanges 104, 105 for pressing against corresponding end sides of an analyser to keep the analyser press fitted within the casing piece 101. The flange 104 may have the function of pressing against a rear end of the analyser. The flange 105 may have the function of pressing against a front end of the analyser, said front end having a portion in which a groove for inserting an analysis strip may be located.

In other examples, more than two flanges differently arranged (e.g. for pressing against respective lateral sides of the analyser) may be used to keep the analyser press fitted within the casing piece 101.

The retaining piece 102 may be movable in such a way that the retaining portion 108a, 108b may be movable between a proximal (or receded) position and a distal (or extended) position relative to the front flange 105 of the casing piece 101, i.e. relative to the groove (for inserting an analysis strip) of an analyser when it is mounted within the casing piece. In the particular case of FIGS. 1 and 2, the retaining portion 108a, 108b is shown in its distal or extended position.

The retaining piece 102 is shown in both Figures comprising a front (retaining) portion compatible with the front flange 105 of the casing piece 101. This front (retaining) portion of the retaining piece 102 may have a first pressing member 108a and a second pressing member 108b both configured to retain (by pressing) the analysis strip during at least part of the movement of the retaining piece 102 between its proximal and distal positions.

These first and second pressing members 108a, 108b may be further adapted to avoid retention of (by not exerting pressure to) the analysis strip at least when the retaining piece 102 is in any of the proximal and distal positions.

The pressing members 108a, 108b may be flexible members such that they can be flexed to a suitable position for laterally pressing (and thus retaining) the strip to be ejected from the analyser. This flexion of the pressing members 108a, 108b may be caused, as commented before, during at least part of the motion of the retaining piece 102 between its proximal and distal positions.

The casing piece 101 may further comprise a guiding element 107a (shown in FIG. 1 but not in FIG. 2) for guiding the pressing member 108a during the motion of the retaining piece 102 between its proximal and distal positions. The casing piece 101 may further comprise a guiding element (not shown in FIGS. 1 and 2) for guiding the other pressing member 108b during the motion of the retaining piece 102 between its proximal and distal positions.

More details about the retaining piece 102, its movement between the proximal and distal positions, and how the pressing members 108a, 108b may accordingly behave are provided in other parts of the description with reference to other Figures.

The casing piece 101 may further comprise a sheet-shaped portion 103 connecting the flanges 104, 105, such that a rear/bottom side of an analyser may be at least partially covered by said sheet-shaped portion 103, when the analyser is press-fitted in the casing piece 101.

The retaining piece 102 may also comprise a sheet-shaped portion (not shown in FIGS. 1 and 2) slidably coupled to the sheet-shaped portion 103 of the casing piece 101. This slidably coupling may be based on a rail based mechanism, a part of which 106 is shown in FIGS. 1 and 2.

Figure 3:
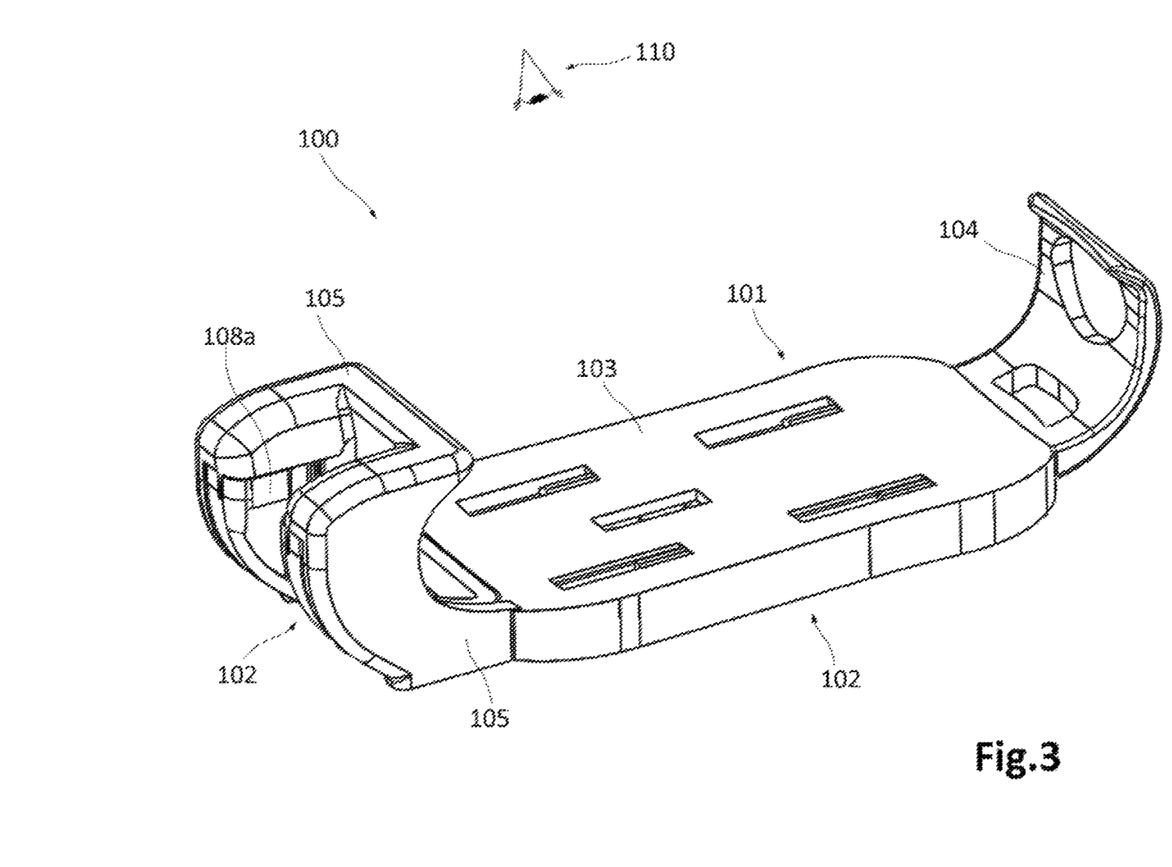
FIG. 3 schematically represents a perspective view of a handgrip similar to the ones shown in FIGS. 1 and 2, wherein its retaining portion is shown in its proximal position.
Figure 4:
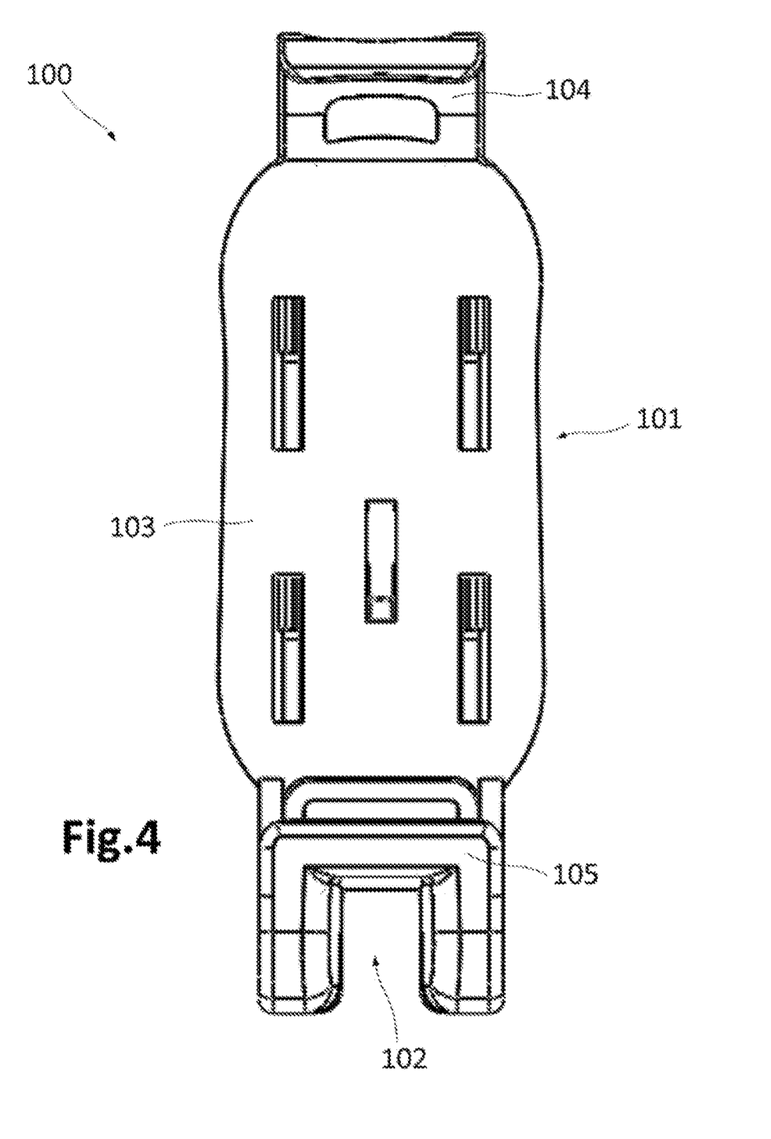
FIG. 4 schematically represents a plan view of a handgrip similar to the ones shown in FIGS. 1-3, with its retaining portion shown in its proximal position.

FIG. 3 schematically represents a perspective view of a handgrip 100 similar to the ones shown in FIGS. 1-2. FIG. 4 schematically represents a plan view of a handgrip 100 similar to the ones shown in FIGS. 1-3. The handgrip 100 is also shown in said FIGS. 3 and 4 comprising a casing piece 101, and a retaining piece 102 having a retaining portion 108a, 108b arranged in its proximal position in these particular views.

The plan view of FIG. 4 may be considered as taken from a top point of vision 110 as indicated in FIG. 3.

A front (retaining) portion of the retaining piece 102 (which is relatively clearly shown in FIGS. 1 and 2) is depicted in FIG. 3 almost completely hidden by a front flange 105 of the casing piece 101. In particular, only one pressing member 108a of said front (retaining) portion of the retaining piece 102 is indicated in FIG. 3. No part of the retaining portion of the retaining piece 102 is shown in FIG. 4, because it appears completely hidden by the front flange 105.

Figure 5:
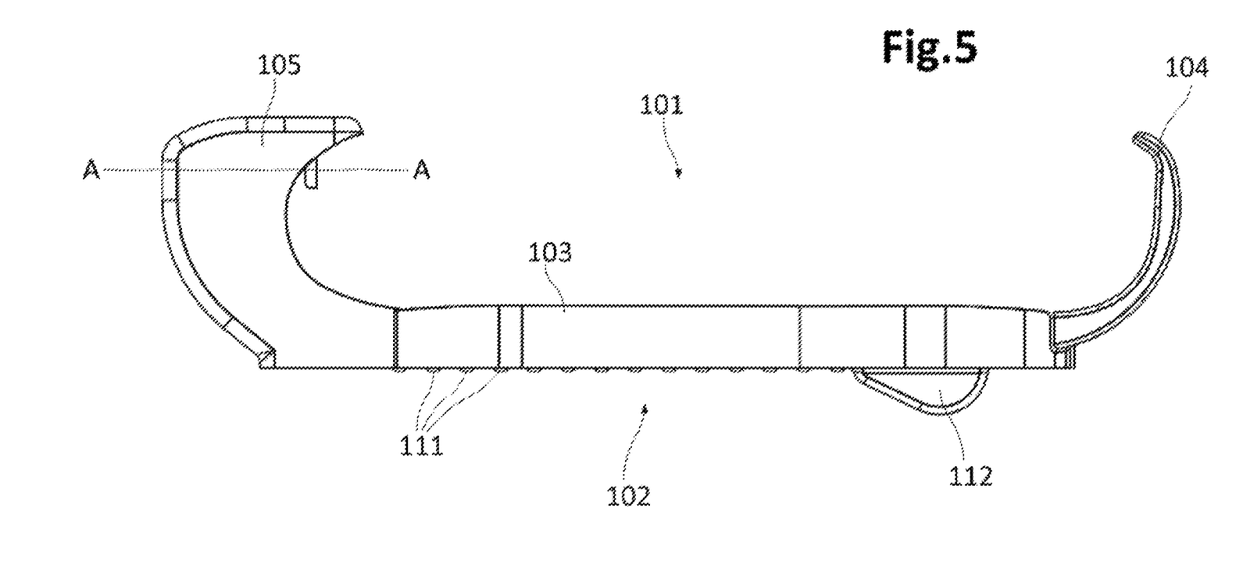
FIG. 5 schematically represents a lateral view of a handgrip similar to the ones shown in FIGS. 1-4, wherein its retaining portion is in its proximal position.

FIG. 5 schematically represents a lateral view of a handgrip 100 similar to the ones shown in FIGS. 1-4. The handgrip 100 is also shown in this example having corresponding casing and retaining pieces 101, 102, the retaining piece 102 being in its proximal (or receded) position.

In this Figure, a plurality of small protuberances 111 and a larger protruding piece 112 are shown as forming part of a sheet-shaped portion of the retaining piece 102, which may be slidably coupled to a sheet-shaped portion 103 of the casing piece 101.

This larger protruding piece 112 and/or this plurality of small protuberances 111 may permit an improved contact by an operator's hand (e.g. fingers) on the sheet-shaped portion of the retaining piece 102. This improved contact may facilitate operation of the handgrip 100 by the operator for moving the retaining piece 102 between its proximal and distal positions.

The casing piece 101 is also shown in FIG. 5 comprising corresponding rear and front flanges 104, 105 for pressing against respective front and rear ends of an analyser to keep it press fitted within the casing piece 101.

Figure 6:
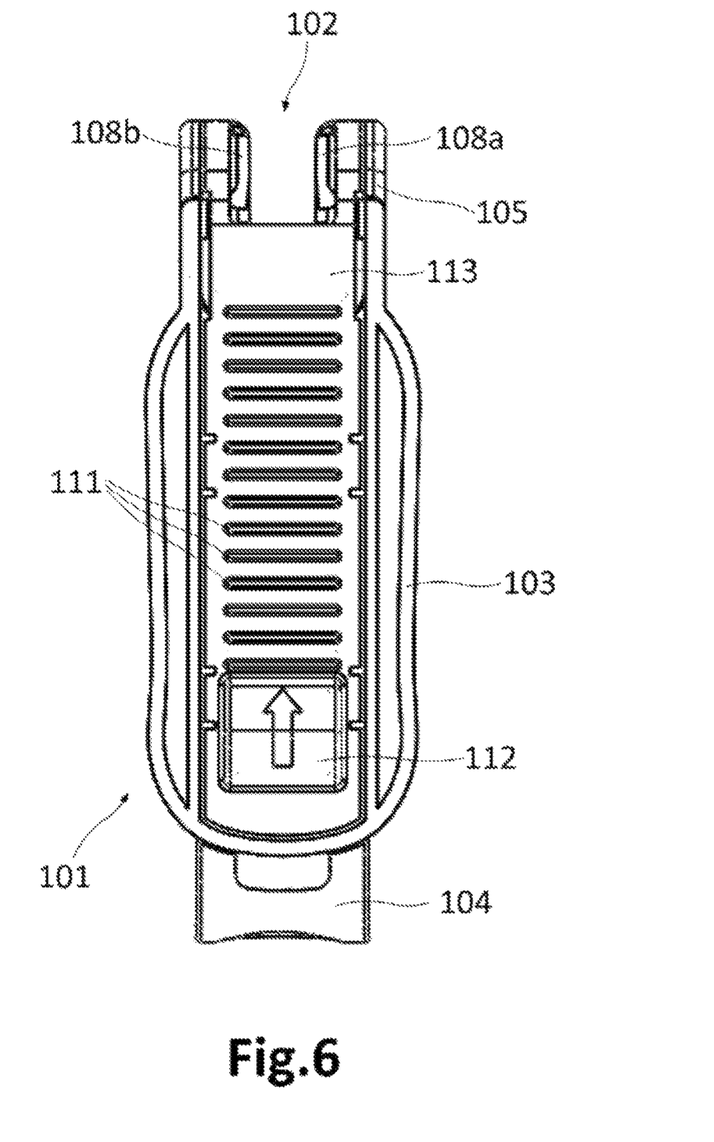
FIG. 6 schematically represents an underside view of a handgrip similar to the ones shown in FIGS. 1-5, with its retaining portion in its proximal position.

FIG. 6 schematically represents an underside view of a handgrip 100 similar to the ones shown in FIGS. 1-5, i.e. from a "bottom" point of vision (not indicated in any of the Figures). The handgrip 100 is shown in this case with its retaining piece 102 in its proximal (or receded) position. This particular view may thus correspond to a handgrip's side opposite to the side shown in FIG. 4.

In FIG. 6, the retaining piece 102 is shown having a sheet-shaped portion 113 similar to the one described with reference to other Figures. In this case, an outer rough surface with small protruding rows 111 and a larger protruding piece 112 is clearly shown for this sheet-shaped portion 113.

The other elements indicated in FIG. 6, such as e.g. front and rear flanges 105, 104 of the casing piece 101, are similarly configured/arranged as described with reference to previous Figures.

Figure 7A:
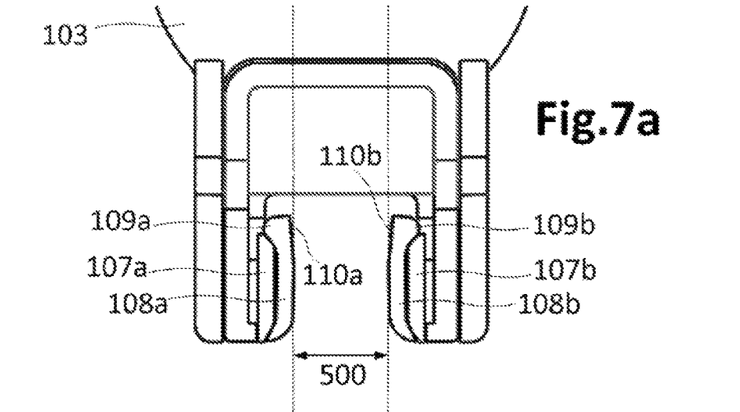
FIG. 7a schematically represents a sectional view of a front part of a handgrip similar to the ones shown in FIGS. 1-6, wherein its retaining portion is shown in its proximal position.
Figure 7B:
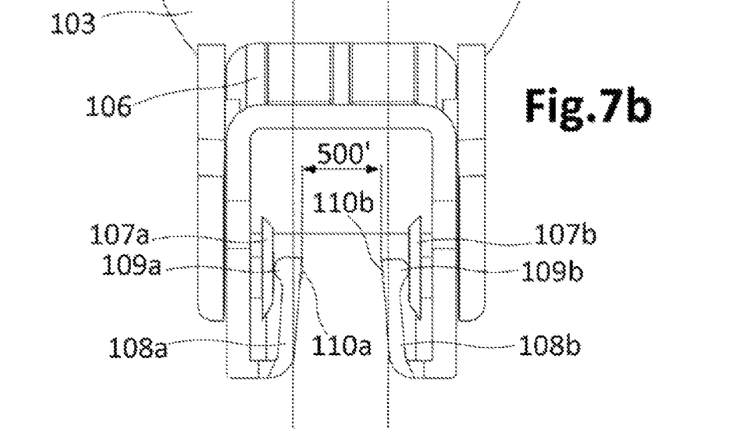
FIG. 7b schematically represents a sectional view of a handgrip's front part similar to the one shown in FIG. 7a, with the handgrip's retaining portion shown in an intermediate position between its proximal and distal positions.
Figure 7C:
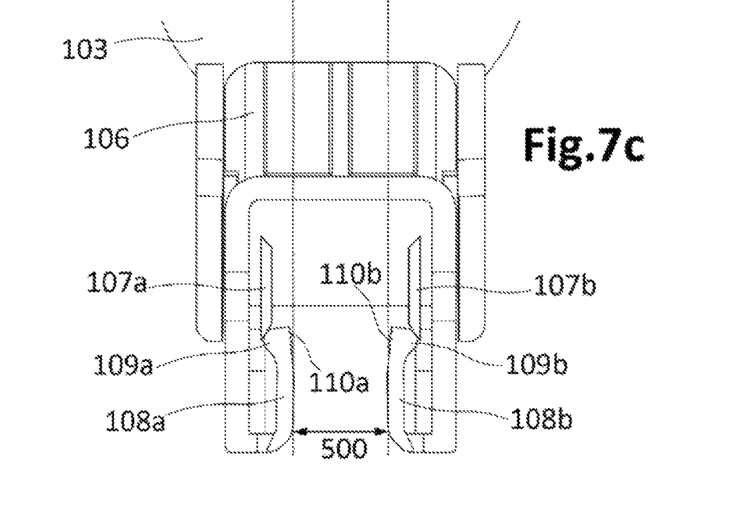
FIG. 7c schematically represents a sectional view of a handgrip's front part similar to the ones shown in FIGS. 7a-7b, wherein the handgrip's retaining portion is shown in its proximal position.

FIGS. 7a-7c show respective sectional views of a front part of a handgrip 100 similar to the ones shown in FIGS. 1-6. This sectional view may be considered as taken according to a plane AA indicated in FIG. 5.

Each of the FIGS. 7a-7c shows first and second pressing members 108a, 108b (of a retaining portion of the handgrip 100) which may be flexible members adapted to be flexed in such a way that they can exert (together) a pressure at corresponding lateral regions of an analysis strip. This pressure that can be exerted to the strip may cause retention of the analysis strip by said pressing members 108a, 108b.

FIG. 7b illustrates a particular condition (during at least part of the motion of the retaining portion from its proximal to the distal position) in which said pressure may be caused. FIGS. 7a and 7c illustrate respective particular conditions (proximal and distal positions of the retaining portion) in which pressure to the strip may be avoided.

As shown in FIGS. 7a-7c, each of the (flexible) pressing members 108a, 108b may comprise respective protruding portions 109a, 109b which may suitably interact with corresponding guiding elements 107a, 107b, which are also shown in said FIGS. 7a-7c.

Each of the flexible pressing members 108a, 108b may comprise a corresponding pressing surface 110a, 110b by which the pressing members 108a, 108b may exert the aforementioned pressure to the analysis strip (to be removed from an analyser suitably coupled with the handgrip 100).

Three different portions may be distinguished in each of the guiding elements 107a, 107b: a first (inner) recess at one end of the guiding element, a second (outer) recess at the opposite end of the guiding element, and a uniform region between said two (inner and outer) recesses.

The expression "inner recess" may refer herein to that recess of a guiding element 107a, 107b which is always in an innermost position of the handgrip 100 irrespective of the (e.g. proximal, distal, intermediate) position of the retaining piece 102.

The expression "outer recess" may refer herein to that recess of a guiding element 107a, 107b which is always in an outermost position of the handgrip 100 irrespective of the (e.g. proximal, distal, intermediate) position of the retaining piece 102.

As shown in FIG. 7a, the protruding region 109a of the pressing member 108a may suitably couple with the inner recess of the guiding element 107a when the retaining piece 102 is in its proximal position. Similarly, the protruding region 109b of the pressing member 108b may also suitably couple with the inner recess of the guiding element 107b when the retaining piece 102 is in its proximal position.

Said coupling of each protruding region 109a, 109b with the inner recess of the corresponding guiding element 107a, 107b may cause the corresponding pressing surfaces 110a, 110b to be separated by a desired distance 500. This distance 500 may be larger than the width of an analysis strip to be ejected, such that no pressure would be exerted by the pressing members 108a, 108b to the analysis strip.

It is worthy of mention that an analysis strip can be easily inserted into a groove of an analyser properly coupled with the handgrip 100, since no opposition is presented by the pressing members 108a, 108b when they are in the position illustrated in FIG. 7a.

As shown in FIG. 7b, the protruding region 109a of the pressing member 108a may suitably contact the uniform region (between the inner and outer recesses) of the guiding element 107a when the retaining piece 102 is in an intermediate position (between the proximal and distal positions) of the retaining piece 102.

Similarly, the protruding region 109b of the pressing member 108b may suitably contact the uniform region (between the inner and outer recesses) of the guiding element 107b when the retaining piece 102 is in an intermediate position (between the proximal and distal positions) of the retaining piece 102.

Said contact of each protruding region 109a, 109b with the uniform region (between the inner and outer recesses) of the corresponding guiding element 107a, 107b may cause the corresponding pressing surfaces 110a, 110b to be separated by a desired distance 500'. This distance 500' may be smaller than the distance 500 (see FIGS. 7a and 7c) and of an amount such that a certain pressure may be exerted by the pressing members 108a, 108b to the analysis strip.

This pressure may thus be continuously exerted to the strip along the entire length of the uniform regions (between the inner and outer recesses) of both guiding elements 107a, 107b. This continuous pressure may cause the pressing members 108a, 108b to retain (i.e. pull) the strip until it is extracted from a corresponding analyser's groove.

As shown in FIG. 7c, the protruding region 109a of the pressing member 108a may suitably couple with the outer recess of the guiding element 107a when the retaining piece 102 is in its distal position. Similarly, the protruding region 109b of the pressing member 108b may also suitably couple with the outer recess of the guiding element 107b when the retaining piece 102 is in its distal position.

Said coupling of each protruding region 109a, 109b with the outer recess of the corresponding guiding element 107a, 107b may cause the corresponding pressing surfaces 110a, 110b to be separated by a desired distance 500. This distance 500 may be larger than the width of an analysis strip to be ejected, such that no pressure would be exerted by the pressing members 108a, 108b to the analysis strip.

The abovementioned continuous pressure exerted by the pressing members 108a, 108b to the strip (as described with reference to FIG. 7b) may be ceased when the pressing members 108a, 108b achieve the condition of FIG. 7c. This way, the strip can be finally released as a result of said cessation of the pressure.

In some or all of the described examples, the handgrip 100 may be manufactured either separated from the analyser or integrated with the analyser. In the former case, the handgrip 100 may be a removable handgrip, such that it may be provided individually. On the contrary, in the latter case, the analyser may be provided with the handgrip 100 as a single piece. Thus, for example, a side of the analyser may coincide with the casing piece of the handgrip.

An aspect of providing a removable handgrip may be that a damaged handgrip may be easily replaced by another in a very easy and cheap manner. Another aspect of providing a removable handgrip may be that a same handgrip may be reused, applied to different analysers of the same type/shape/size. Of course, different sizes/shapes for the removable handgrip may be taken into account depending on the model of analyser with which the handgrip is intended to be used.

Although only a number of particular examples of the invention have been disclosed herein, it will be understood by those skilled in the art that other alternative examples and/or uses of the invention and obvious modifications and equivalents thereof are possible. Furthermore, the present invention covers all possible combinations of the particular examples described. Thus, the scope of the present invention should not be limited by particular examples, but should be determined only by a fair reading of the claims that follow.

The invention claimed is:

1. A handgrip configured to extract an analysis strip from a groove of an analyser, the handgrip comprising:
    a casing piece configured to be attached with the analyser; and
    a retaining piece having a retaining portion, the retaining piece being movable with respect to the casing piece in such a way that the retaining portion is movable in a first direction from a proximal position to a distal position relative to the casing piece;
    wherein:
    the retaining portion is configured to retain the analysis strip during at least part of its movement from the proximal to the distal position, and to avoid retaining the analysis strip at least when the retaining portion is in any of the proximal and distal positions.

2. A handgrip according to claim 1, wherein:
    the retaining portion comprises a pressing arrangement;
    the pressing arrangement is configured to exert pressure to the analysis strip, thereby causing the retention of the analysis strip, during the at least part of the movement of the retaining portion from the proximal to the distal position; and
    the pressing arrangement is configured to avoid exerting pressure to the analysis strip, thereby causing the avoidance of retention of the analysis strip, at least when the retaining portion is in any of the proximal and distal positions.

3. A handgrip according to claim 2, wherein:
    the pressing arrangement comprises a first and a second pressing member facing each other and defining a path having a distance between them, said path being perpendicular to the first direction;
    the first and second pressing members are configured to reduce the distance between them, thereby causing the exertion of pressure to the analysis strip, during the at least part of the movement of the retaining portion from the proximal to the distal position; and
    the first and second pressing members are configured to increase the distance between them, thereby causing the avoidance of exertion of pressure to the analysis strip, at least when the retaining portion is in any of the proximal and distal positions.

4. A handgrip according to claim 3, wherein the first and second pressing members are arranged in such a way that the distance reduction causes the exertion of pressure to the analysis strip at corresponding first and second lateral regions of the analysis strip, during the at least part of the movement of the retaining portion from the proximal to the distal position.

5. A handgrip according to claim 3, wherein at least one of the first and second pressing members is a flexible member configured to be flexed to a compressed position for causing the distance reduction during the at least part of the movement of the retaining portion from the proximal to the distal position, and to be flexed to a relaxed position for causing the distance increase at least when the retaining portion is in any of the proximal and distal positions.

6. A handgrip according to claim 5, wherein both the first and second pressing members are flexible members configured to be flexed to the compressed position for causing the distance reduction during the at least part of the movement of the retaining portion from the proximal to the distal position, and to be flexed to the relaxed position for causing the distance increase at least when the retaining portion is in any of the proximal and distal positions.

7. A handgrip according to claim 5, wherein the casing piece comprises a guiding piece for each flexible pressing member respectively, each guiding piece being configured to guide its corresponding flexible pressing member to the compressed position for causing the distance reduction during the at least part of the movement of the retaining portion from the proximal to the distal position, and to guide its corresponding flexible pressing member to the relaxed position for causing the distance increase at least when the retaining portion is in any of the proximal and distal positions.

8. A handgrip according to claim 1, wherein the casing piece is configured to be removably attached with the analyser in a press-fitting manner.

9. A handgrip according to claim 8, wherein the casing piece comprises at least two flanges configured to press against corresponding end sides of the analyser respectively, in such a way that the analyser can be press-fitted within the casing piece.

10. A handgrip according to claim 9, wherein the casing piece comprises a sheet-shaped portion connecting the at least two flanges and being configured to at least partially cover a rear/bottom side of the analyser when the analyser is press-fitted within the casing piece.

11. A handgrip according to claim 10, wherein the retaining piece comprises a sheet-shaped portion slidably coupled to the sheet-shaped portion of the casing piece.

12. A handgrip according to claim 11, further comprising a rail based mechanism; wherein the sheet-shaped portion of the retaining piece is slidably coupled with the sheet-shaped portion of the casing piece by said rail based mechanism.

13. A handgrip according to claim 11, wherein the sheet-shaped portion of the retaining piece has an external rough surface.

14. An analyser comprising:
    a groove for inserting an analysis strip; and
    a handgrip configured to extract the analysis strip from the groove, according to claim 1.

15. An analyser according to claim 14, further comprising the analysis strip inserted in the groove.

\* \* \* \* \*